(12) United States Patent
Rogers et al.

(10) Patent No.: US 12,408,910 B2
(45) Date of Patent: Sep. 9, 2025

(54) HEALICOIL KNOTLESS DISTAL TIP AND PLUG TRANSMISSION

(71) Applicants:Smith & Nephew, Inc., Memphis, TN (US); Smith & Nephew Orthopaedics AG, Zug (CH); Smith & Nephew Asia Pacific Pte. Limited, Singapore (SG)

(72) Inventors: Jon-Paul Rogers, North Smithfield, RI (US); Mark Edwin Housman, North Attleborough, MA (US); Richard Perry Rego, Jr., Mansfield, MA (US); Peter James Cashmore, Durham, NH (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 218 days.

(21) Appl. No.: 17/026,893

(22) Filed: Sep. 21, 2020

(65) Prior Publication Data

US 2021/0128137 A1 May 6, 2021

Related U.S. Application Data

(60) Provisional application No. 62/928,576, filed on Oct. 31, 2019.

(51) Int. Cl.
*A61B 17/04* (2006.01)
*A61B 17/00* (2006.01)
(52) U.S. Cl.
CPC ............... *A61B 17/0401* (2013.01); *A61B 2017/00004* (2013.01); *A61B 2017/0412* (2013.01);
(Continued)

(58) Field of Classification Search
CPC ...... A61B 17/0401; A61B 2017/00004; A61B 2017/0412; A61B 2017/0414;
(Continued)

(56) References Cited

U.S. PATENT DOCUMENTS 9,526,488 B2 * 12/2016 Arai ................... A61B 17/0401
2003/0187446 A1 * 10/2003 Overaker ........... A61B 17/0401
606/232

(Continued)

FOREIGN PATENT DOCUMENTS

CN 108135595 A 8/2018
WO WO-2011060022 A2 * 5/2011 ......... A61B 17/0401
(Continued)

OTHER PUBLICATIONS

European Application No. 20789310.8-1122, Examination Report, dated Jul. 11, 2024.
(Continued)

*Primary Examiner* — Brooke Labranche
(74) *Attorney, Agent, or Firm* — ArentFox Schiff LLP; Joseph M. Maraia; Marlo Schepper Grolnic

(57) ABSTRACT

An anchor assembly can include an anchor comprising a proximal portion, a distal portion having a tip, and a surface extending between the tip and the proximal portion and can include a protrusion extending along a length of the surface. The anchor can define a cavity therein with a wall of the cavity having threads, an opening to the cavity located in the proximal anchor portion, and a through hole defined in a distal portion of the tip. Further, the anchor assembly can include a plug having a threaded proximal outer portion and a non-threaded distal outer portion disposed within the cavity of the anchor. The threaded proximal outer portion can be engaged with the cavity wall threads and the non-threaded distal outer portion can be configured to move (Continued)

axially within the anchor cavity. The anchor assembly can include a sleeve having an opening to receive the protrusion.

9 Claims, 3 Drawing Sheets

(52) U.S. Cl.
CPC . *A61B 2017/0414* (2013.01); *A61B 2017/044* (2013.01); *A61B 2017/0441* (2013.01); *A61B 2017/0445* (2013.01); *A61B 2017/0453* (2013.01); *A61B 2017/0464* (2013.01)

(58) Field of Classification Search
CPC ...... A61B 2017/044; A61B 2017/0441; A61B 2017/0445; A61B 2017/0453; A61B 2017/0464; A61B 2017/0409
See application file for complete search history.

(56) References Cited

U.S. PATENT DOCUMENTS

| 2007/0270855 | A1* | 11/2007 | Partin | A61B 17/863 |
| | | | | 606/279 |
| 2009/0112270 | A1* | 4/2009 | Lunn | A61B 17/0401 |
| | | | | 606/301 |
| 2010/0262185 | A1 | 10/2010 | Gelfand et al. | |
| 2011/0112576 | A1* | 5/2011 | Nguyen | A61B 17/0401 |
| | | | | 606/232 |
| 2014/0277129 | A1 | 9/2014 | Arai et al. | |
| 2016/0113643 | A1 | 4/2016 | Diduch et al. | |
| 2018/0185019 | A1 | 7/2018 | Lunn et al. | |

FOREIGN PATENT DOCUMENTS

| WO | 2017011185 A1 | 1/2017 |
| WO | 2017199152 A1 | 11/2017 |
| WO | 2019108222 A1 | 6/2019 |
| WO | 2019108224 A1 | 6/2019 |
| WO | 2019217970 A1 | 11/2019 |

OTHER PUBLICATIONS

International Search Report and Written Opinion for International Application No. PCT/US20/051788, International Filing Date Sep. 21, 2020, Date of Mailing Dec. 21, 2020, 14 pages.

* cited by examiner

HEALICOIL KNOTLESS DISTAL TIP AND PLUG TRANSMISSION

CROSS-REFERENCE TO RELATED APPLICATIONS

This application claims priority to U.S. Provisional Application No. 62/928,576, entitled "HEALICOIL KNOTLESS DISTAL TIP AND PLUG TRANSMISSION," filed on Oct. 31, 2019, the entire contents of which are hereby incorporated by reference.

TECHNICAL FIELD

The described technology relates generally to tissue repair, and more specifically, to an anchor for securing tissue to bone.

BACKGROUND

Arthroscopic procedures often require soft tissue to be reattached to bone. To achieve this, anchors are placed in the bone and sutures attached to the anchor are passed through the tissue to securely retain the tissue in place. When making a repair of soft tissue to bone, it is advantageous to have as large an area of contact between the bone and tissue as possible. Anchor points spaced from one another in rows result in a repair having a broader area of contact.

SUMMARY

A procedure, and components for use in such procedure, that securely attaches tissue to bone using a plurality of attachment points over a large area of contact is needed. Such procedure must be able to be done in a quick and efficient manner with a minimum of recovery time for the patient.

In one aspect, the present disclosure relates to an anchor assembly for securing tissue to bone. The anchor assembly can include an anchor having a proximal portion, a distal portion having a tip, and a surface extending between the tip and the proximal portion. The surface can include a protrusion extending along a length of the surface. The anchor can define a cavity therein with a wall of the cavity having threads. Further, the anchor can have an opening to the cavity located in the proximal anchor portion and a through hole defined in a distal portion of the tip. Further, the anchor assembly can include a plug having a threaded proximal outer portion and a non-threaded distal outer portion disposed within the cavity of the anchor. The threaded proximal outer portion can be engaged with the cavity wall threads and the non-threaded distal outer portion can be configured to move axially within the anchor cavity. Further, the anchor assembly can include a sleeve having an opening to receive the protrusion. The sleeve can be releasably coupled to the anchor and disposed about the surface at the proximal portion of the anchor. Further, the protrusion and the opening are configured to reduce the rotation of the anchor with respect to the sleeve.

In some embodiments, the plug can include an internal cavity having a proximal inner portion. The proximal inner portion can include at least one of a D-shape, a triangle shape, a rectangle shape, a square shape, and a star shape.

In some embodiments, the anchor includes a plurality of protrusions extending along a length of the surface. In some embodiments, the sleeve can include a plurality of openings. Each opening is configured to receive the respective plurality of protrusions. The sleeve can include an internal cavity having a distal inner portion. The distal inner portion has at least one of a D-shape, a triangle shape, a rectangle shape, a square shape, and a star shape. In some embodiments, the sleeve can include an internal cavity having a threaded distal inner portion. The threaded distal inner portion can have a similar shape as the proximal outer portion of the plug.

In one aspect the present disclosure relates to a method of tissue repair. The method can include driving an anchor assembly of an anchor system into a bone hole with an anchor driver. The anchor system can include a sleeve. The sleeve can include at least one open helical coil having a proximal end and a distal end wherein the at least one open helical coil defines an internal volume communicating with a region exterior to the at least one open helical coil through a spacing between turns of the at least one open helical coil. The sleeve can further include at least one rib disposed within the internal volume, connected to at least two turns of the at least one open helical coil, wherein the at least one rib is engageable with a grooved outer shaft of the anchor driver. The anchor assembly is engageable with the sleeve. The anchor assembly can include an anchor comprising a proximal portion, a distal portion having a tip, and a surface extending between the tip and the proximal portion, the surface including a protrusion extending along a length of the surface, the anchor defining a cavity therein, with a wall of the cavity having threads, and the anchor having an opening to the cavity located in the proximal anchor portion and a through hole defined in a distal portion of the tip. The anchor assembly can also include a plug, having a threaded proximal outer portion and a non-threaded distal outer portion, disposed within the cavity of the anchor, wherein the threaded proximal outer portion is engaged with the cavity wall threads and the non-threaded distal outer portion is configured to move axially within the anchor cavity. The sleeve has an opening to receive the protrusion, releasably coupled to the anchor and disposed about the surface at the proximal portion of the anchor, wherein the protrusion and the opening are configured to reduce the rotation of the anchor with respect to the sleeve.

The method can further include advancing the sleeve into the bone and into engagement with the anchor assembly using the anchor driver. The anchor driver further includes an axially compliant member configured to allow a relative motion between the grooved outer shaft and an inner shaft along a longitudinal axis of the anchor driver. The axially compliant member can be separate and distinct from a spring of the torque and/or travel limiter.

The method can further include advancing, using the anchor driver, the plug into a distal suture-locked position to capture the suture in a locked position. The method can also include a retracting, using the anchor driver, the plug into a proximal, suture unlocked position to release the suture into a freely slidable state.

In some embodiments, the method includes engaging the at least one rib of the sleeve with the grooved outer shaft of the anchor drive, engaging the suture capture member of the tip structure with the inner shaft of the anchor driver, and releasably attaching the tip structure to an intermediate shaft of the anchor driver positioned between the grooved outer shaft and the inner shaft.

The method can include exerting a threshold force along a longitudinal axis of the anchor driver, causing a retraction of the grooved outer shaft of the anchor driver. Further, the method can include advancing the sleeve further comprises axially sliding the sleeve along a longitudinal axis of the anchor driver. The anchor driver further can include a housing defining a threaded internal cavity coupled with the grooved outer shaft for providing a threaded travel of the sleeve relative to the inner shaft, wherein advancing the sleeve is achieved by rotating the housing. The housing can be slidable relative to the inner shaft along the longitudinal axis of the anchor driver for providing a slidable travel of the sleeve.

In some embodiments, the slidable travel of the sleeve is equal to or greater than an axial clearance defined along the longitudinal axis of the anchor driver between a surface of the bone and a distal end of the sleeve, the sleeve being substantially engaged with the grooved outer shaft. In other embodiments, a combined travel of the sleeve includes the slidable travel of the sleeve added to the threaded travel of the sleeve, is equal to or greater than the axial clearance.

In some embodiments, at least one of the sleeve, the housing, or the grooved outer shaft further includes one or more locking mechanisms for preventing a longitudinal sliding motion of the housing.

BRIEF DESCRIPTION OF THE DRAWINGS

Various aspects of at least one embodiment of the present disclosure are discussed below with reference to the accompanying figures. It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. For purposes of clarity, not every component may be labeled in every drawing. The figures are provided for the purposes of illustration and explanation and are not intended as a definition of the limits of the invention.

DETAILED DESCRIPTION

Figure 1A:
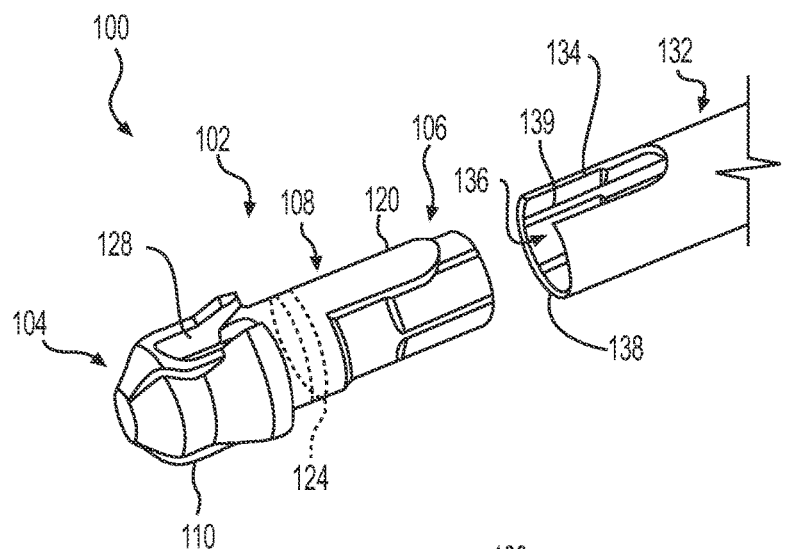
FIGS. 1A-1B illustrate an anchor assembly, according to certain embodiments.

In the following detailed description, numerous specific details are set forth in order to provide a thorough understanding of the embodiments of the present disclosure. It will be understood by those of ordinary skill in the art that these embodiments may be practiced without some of these specific details. In other instances, well-known methods, procedures, components and structures may not have been described in detail so as not to obscure the described embodiments.

Prior to describing at least one embodiment in detail, it is to be understood that the claims are not limited in their application to the details of construction and the arrangement of the components set forth in the following description or illustrated in the drawings. Also, it is to be understood that the phraseology and terminology employed herein are for the purpose of description only and should not be regarded as limiting.

During an arthroscopic procedure, an implant is delivered to a bone hole to secure soft tissue. The present disclosure describes an assembly which consists of a two piece implant, a distal tip and a proximal body. The distal tip can be secured to an inserter middle shaft described in U.S. Pat. No. 9,526,488, incorporated herein by reference. The distal tip can include sutures which pass through an eyelet and is inserted into a prepped or no-prepped hole before delivering the proximal body. The distal plug allows for torsional loads which will allow for the suture to be adequately captured in the eyelet.

The present disclosure provides an anchor assembly for securing tissue to bone. The anchor assembly provides a transmission feature between the distal plug and inner shaft which can provide adequate torsional strength to capture the suture.

Figure 1B:
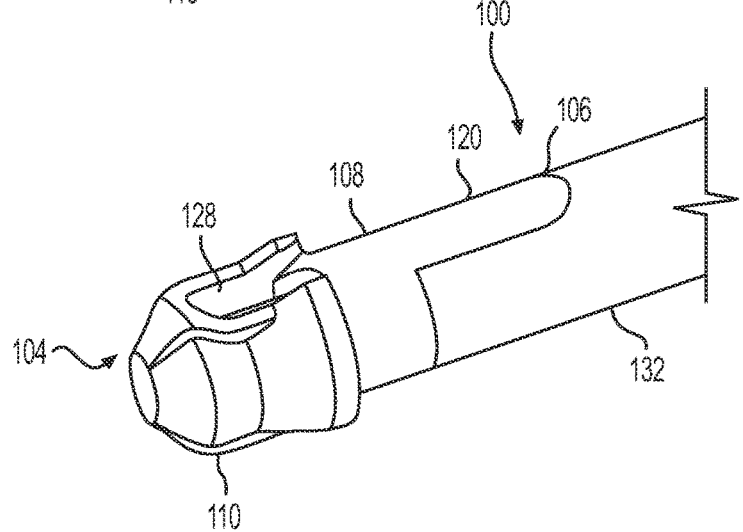

FIG. 1A illustrates an anchor assembly 100 being disassembled, according to certain embodiments. FIG. 1B illustrates the anchor assembly 100 in assembled position, according to certain embodiments, for delivering to a bone hole. The anchor assembly 100 includes an anchor 102. The anchor 102 has a proximal portion 106 and a distal portion 104. The distal portion 104 includes a tip 110. The distal end of the tip 110 may be blunt, as shown, or may be pointed. The tip 110 can be constructed from, for example but not limited to, polymers (e.g., PEEK), bioabsorbable materials, metals (e.g., surgical steel, titanium), or any other suitable material. The anchor 102 also includes a surface 108 extending between the tip 110 and the proximal portion 106. The surface 108 includes a protrusion 120 extending along a length of the surface 108. The protrusion 120 can have any geometrical shape. In some embodiments, the protrusion 120 has a semi-oval shape. Further, the anchor 102 defines a cavity 122 therein, with a wall of the cavity 122 having threads 124. The anchor 102 includes an opening 126 to the cavity 122 located in the proximal anchor portion 106. The anchor 102 can include a through hole 128 defined in a distal portion 104 of the tip 110.

As FIGS. 1A-1B illustrate, the anchor assembly 100 includes a plug 340 (FIG. 4) having a threaded proximal outer portion 342 and a non-threaded distal outer portion 344, disposed within the cavity 122 (FIG. 2) of the anchor 102. The threaded proximal outer portion 342 is engaged with the cavity wall threads 124 and the non-threaded distal outer portion 344 is configured to move axially within the anchor cavity 122.

Further, the anchor assembly 100 can include a sleeve 132 having an opening 134 for receiving the protrusion 120, as shown in FIGS. 1A-1B. The sleeve 132 may have an open helical coil configuration, as described in U.S. Pat. No. 9,526,488, incorporated herein by reference. The sleeve 132 can be constructed from, for example but not limited to, polymers (e.g., PEEK), bioabsorbable materials, metals (e.g., surgical steel, titanium), or any other suitable material. The opening 134 can be releasably coupled to the anchor 102 and disposed about the surface 108 at the proximal portion 106 of the anchor 102. The sleeve 132 includes an internal cavity 136 having a distal inner portion 138. The distal inner portion 138 of the sleeve 132 includes a threaded surface 139. In some embodiments, the threaded surface 139 has the same or similar shape as the proximal portion 106 of the anchor 102. The protrusion 120 and the opening 134 are configured to reduce the rotation of the anchor 102 with respect to the sleeve 132.

Figure 2:
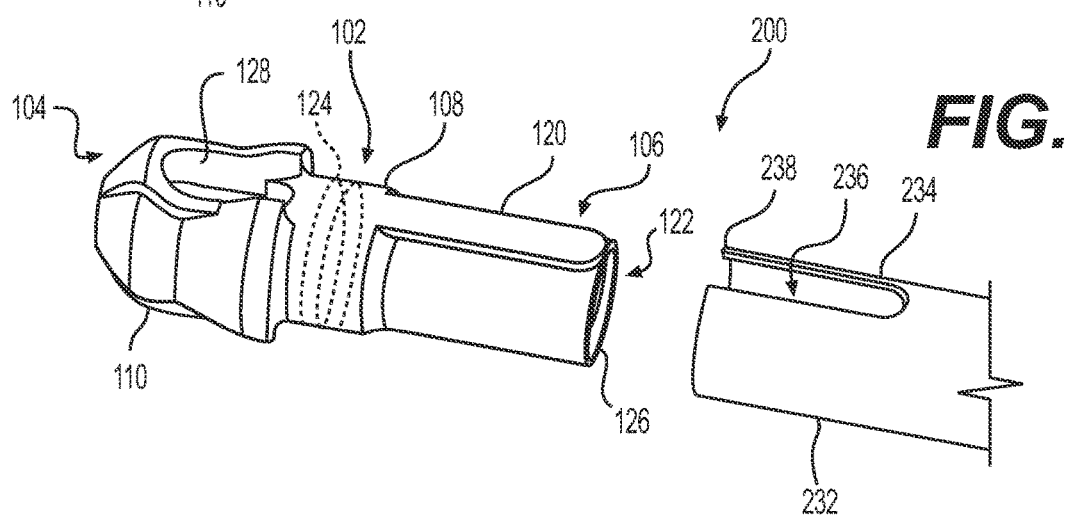
FIG. 2 illustrates an anchor of the anchor assembly, according to certain embodiments.

FIG. 2 illustrates an anchor assembly 200, according to certain embodiments. Similar to anchor assembly 100, the anchor assembly 200 includes an anchor 102. The anchor 102 has a proximal portion 106 and a distal portion 104. The distal portion 104 includes a tip 110. The anchor 102 also includes a surface 108 extending between the tip 110 and the proximal portion 106. The surface 108 includes a protrusion 120 extending along a length of the surface 108. Further, the anchor 102 defines a cavity 122 therein, with a wall of the cavity 122 having threads 124. The anchor 102 includes an opening 126 to the cavity 122 located in the proximal anchor portion 106. The anchor 102 can include a through hole 128 defined in a distal portion 104 of the tip 110.

As FIG. 2 illustrates the anchor assembly 200 includes a plug 340 (FIG. 4) having a threaded proximal outer portion 342 and a non-threaded distal outer portion 344, disposed within the cavity 122 of the anchor 102. The threaded proximal outer portion 342 is engaged with the cavity wall threads 124 and the non-threaded distal outer portion 344 is configured to move axially within the anchor cavity 122.

The anchor assembly 200 can include a sleeve 232 having an opening 234 for receiving the protrusion 120, as shown in FIG. 2. The opening 234 can be releasably coupled to the anchor 102 and disposed about the surface 108 at the proximal portion 106 of the anchor 102. The sleeve 232 includes an internal cavity 236 having a distal inner portion 238. The distal inner portion 238 of the sleeve 232 includes the same or similar shape as the proximal portion 106 of the anchor 102. As explained above, the protrusion 120 and the opening 234 are configured to reduce the rotation of the anchor 102 with respect to the sleeve 232.

Figure 3A:
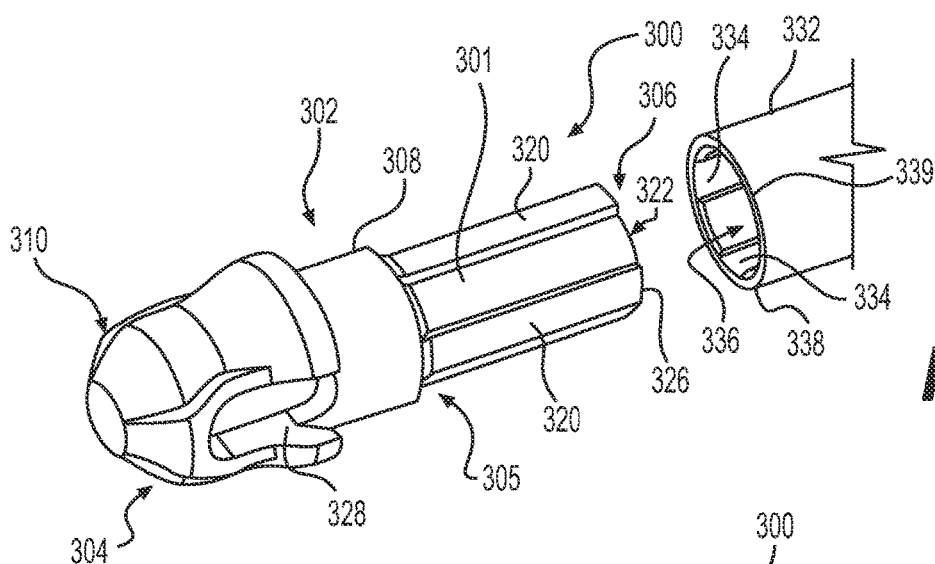
FIG. 3A-3B illustrate an anchor assembly, according to certain embodiments.
Figure 3B:
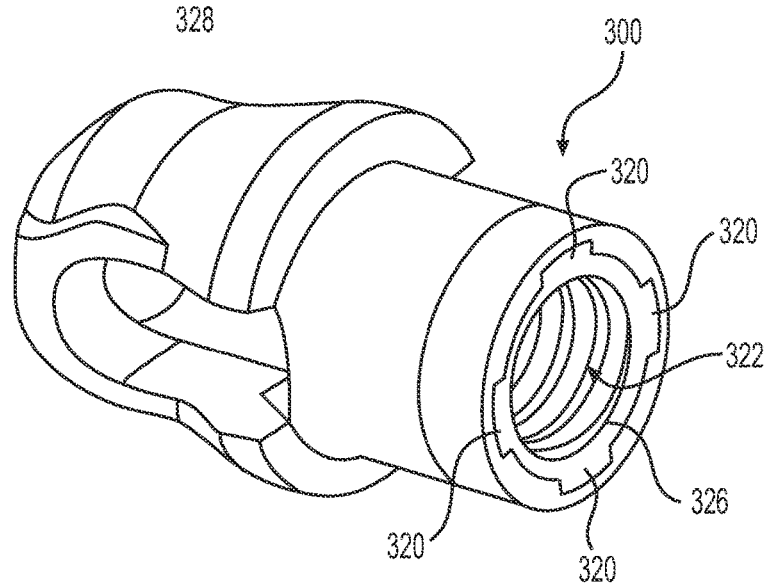
Figure 4:
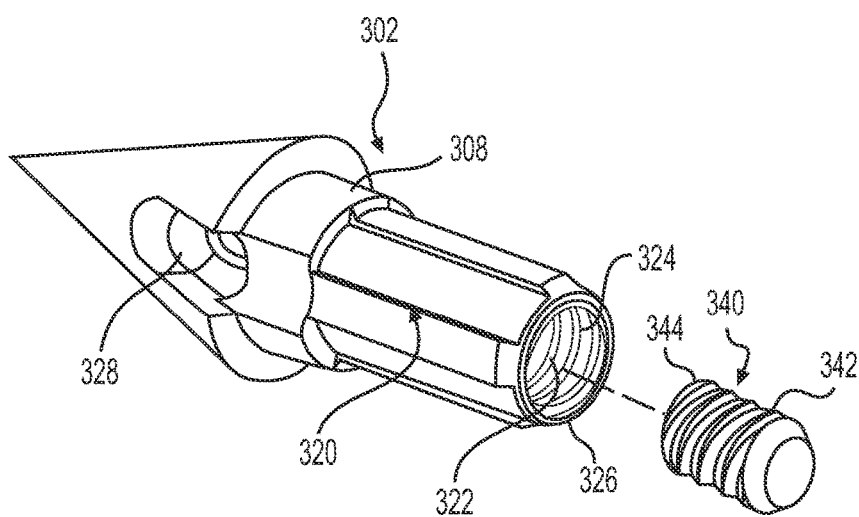
FIG. 4 illustrates an anchor of the anchor assembly of FIGS. 3A-3B, according to certain embodiments.

FIGS. 3A-3B illustrate an anchor assembly 300, according to certain embodiments. FIG. 3A illustrates an anchor assembly 300 being disassembled, according to certain embodiments. FIG. 3B illustrates the anchor assembly 300 in assembled position, according to certain embodiments. FIG. 4 illustrates an anchor 302 of the anchor assembly 300, according to certain embodiments. The anchor assembly 300 includes an anchor 302. The anchor 302 has a proximal portion 306, a distal portion 304, and a middle portion 305. The distal portion 304 includes a tip 310. The distal end of the tip 310 may be blunt, as shown in FIG. 3A, or may be pointed as shown in FIG. 4. The anchor 302 also includes a first surface 308 extending between the tip 310 and the middle portion 305. Further, the anchor 302 includes a second surface 301 extending from the middle portion 305 to the proximal portion 306. The second surface 301 includes a plurality of protrusions 320 extending along a length of the second surface 301 from the middle portion 305 to the proximal portion 306.

In some embodiments, the second surface 301 includes four protrusions 320. The plurality of protrusions 320 can have any geometrical shape. In some embodiments, the plurality of protrusions 320 has a rectangular shape. Further, the anchor 302 defines a cavity 322 therein having an internal axis extending from the distal portion 304 to the proximal portion 306. The second surface 301 is located closer to the internal axis than the first surface 308. A wall of the cavity 322 has threads 324. The anchor 302 includes an opening 326 to the cavity 322 located in the proximal anchor portion 306. The anchor 302 can include a through hole 328 defined in a distal portion 304 of the tip 310.

The anchor assembly 300 can include a plug 340 having a threaded proximal outer portion 342 disposed within the cavity 322 of the anchor 302. The threaded proximal outer portion 342 is engaged with the cavity wall threads 324.

Further, the anchor assembly 300 can include a sleeve 332 having an internal cavity 336 with a distal inner portion 338 having an inner surface 339. The inner surface 339 includes a plurality of openings 334 for receiving the plurality of protrusions 320, as shown in FIGS. 3A-3B. Each opening of the plurality of openings 334 receives the respective protrusion of the plurality of protrusions 320. The plurality of openings 334 can be releasably coupled to the anchor 302 and disposed about the second surface 301 at the middle portion 305 of the anchor 302. The plurality of protrusions 320 and the plurality of openings 334 are configured to reduce the rotation of the anchor 302 with respect to the sleeve 332.

Figure 5:
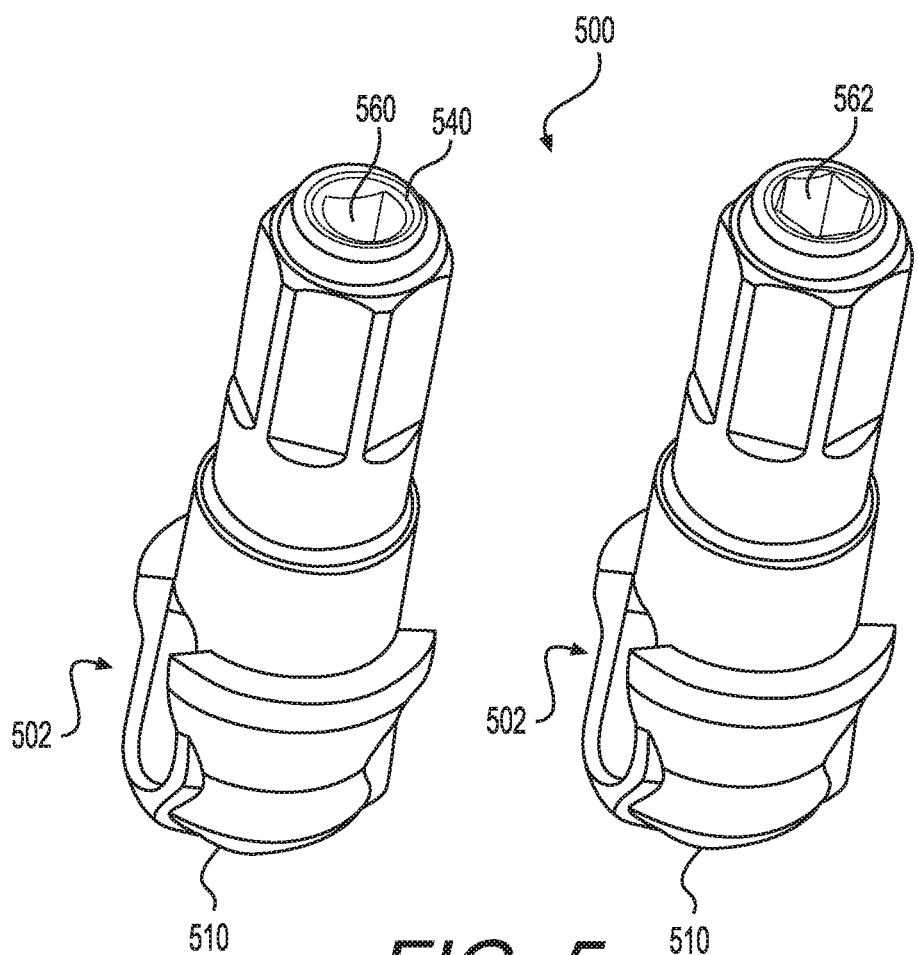
FIG. 5 illustrates an anchor of the anchor assembly, according to certain embodiments.
Figure 6:
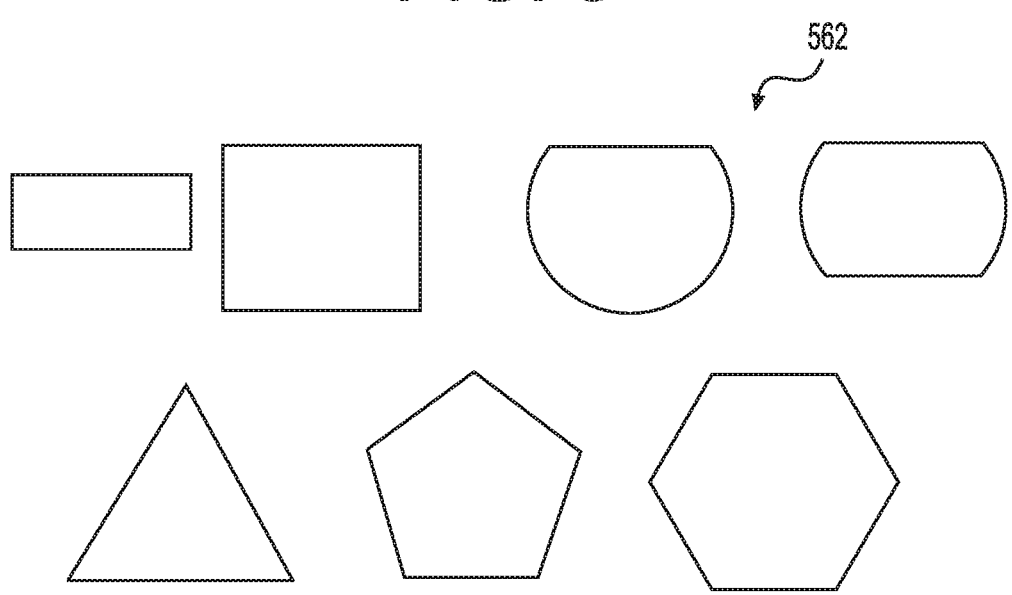
FIG. 6 illustrates cross sectional surface of an internal cavity of a plug of the anchor assembly, according to certain embodiments.

FIG. 5 illustrates an anchor 502 having a tip 510 and a plug 540, according to certain embodiments. The distal end of the tip 510 may be blunt, as shown, or may be pointed. As FIG. 5 illustrates, the plug 540 includes an internal cavity 560 having a proximal inner portion 562. The proximal inner portion 562 includes a D-shape surface. In some embodiments, the proximal inner portion 562 of the internal cavity 560 can include a triangle shape, a rectangle shape, a square shape, and a star shape (shown in FIG. 6).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Whereas many alterations and modifications of the disclosure will no doubt become apparent to a person of ordinary skill in the art after having read the foregoing description, it is to be understood that the particular embodiments shown and described by way of illustration are in no way intended to be considered limiting. Further, the subject matter has been described with reference to particular embodiments, but variations within the spirit and scope of the disclosure will occur to those skilled in the art. It is noted that the foregoing examples have been provided merely for the purpose of explanation and are in no way to be construed as limiting of the present disclosure.

Although the present disclosure has been described herein with reference to particular embodiments, the present disclosure is not intended to be limited to the particulars disclosed herein; rather, the present disclosure extends to all functionally equivalent structures, methods and uses, such as are within the scope of the claims.

The invention claimed is:

1. An anchor assembly comprising:
   an anchor comprising a proximal portion and a distal portion, the distal portion having a tip defining a through hole extending through a width of the anchor for receiving a suture therethrough, an outer lateral surface of the proximal portion including a protrusion defined by a circumferential portion, and a single elongate portion extending from the circumferential portion towards a proximal end of the anchor, a surface of both the circumferential portion and the single elongate portion being raised relative to an entirety of a remainder of the outer lateral surface of the proximal portion, the anchor defining a cavity therein, a wall of the cavity having threads, the anchor having an opening to the cavity located in the proximal portion;
   a plug having a threaded proximal outer portion and a non-threaded distal outer portion, the plug disposed within the cavity of the anchor such that the threaded proximal outer portion is engaged with the cavity wall threads and the non-threaded distal outer portion is configured to move axially within the anchor cavity; and a sleeve having an opening to engage the single elongate portion, the sleeve releasably coupled to the anchor and disposed about the outer lateral surface at the proximal portion of the anchor when the sleeve is engaged with the single elongate portion, the engagement of the sleeve with the single elongate portion preventing rotation of the sleeve relative to the anchor in both a clockwise and counterclockwise direction;

wherein the single elongate portion and the opening are configured to reduce the rotation of the anchor with respect to the sleeve;

wherein the entirety of the remainder of the outer lateral surface of the proximal portion comprises a majority of the outer lateral surface of the proximal portion;

wherein a proximal end of the single elongate portion is distal to a proximal-most end of the remainder of the outer lateral surface of the proximal portion of the anchor; and wherein the through hole is distal to the circumferential portion of the protrusion.

2. The anchor assembly of claim 1, wherein the plug comprises an internal cavity having a proximal inner portion, the proximal inner portion comprises at least one of a D-shape, a triangle shape, a rectangle shape, a square shape, and a star shape.

3. The anchor assembly of claim 1, wherein the sleeve comprises an internal cavity having a distal inner portion, the distal inner portion comprises at least one of a D-shape, a triangle shape, a rectangle shape, a square shape, and a star shape.

4. The anchor assembly of claim 1, wherein the sleeve comprises an internal cavity having a threaded distal inner portion, the threaded distal inner portion having a similar shape as the proximal outer portion of the plug.

5. The anchor assembly of claim 1, wherein a distal end of the tip is blunt.

6. The anchor assembly of claim 1, wherein a distal end of the tip is pointed.

7. The anchor assembly of claim 1, wherein the single elongate portion has a semi-oval shape.

8. The anchor assembly of claim 1, wherein at least one of the tip and the sleeve comprises polymers, bioabsorbable materials, or metals.

9. The anchor assembly of claim 1, wherein the protrusion is non-threaded.

* * * * *